United States Patent [19]

Beckers et al.

[11] 4,433,146

[45] Feb. 21, 1984

[54] PROCESS FOR THE PREPARATION OF MELAMINE

[75] Inventors: Jozeph H. M. Beckers, Heerlen; Rudolf Sipkema, Geleen, both of Netherlands

[73] Assignee: Stamicarbon B.V., Geleen, Netherlands

[21] Appl. No.: 368,972

[22] Filed: Apr. 16, 1982

[30] Foreign Application Priority Data

Apr. 7, 1982 [NL] Netherlands ............... 8201480

[51] Int. Cl.$^3$ ........................................... C07D 251/60
[52] U.S. Cl. ................................................. 544/201
[58] Field of Search .......................................... 544/201

[56] References Cited

U.S. PATENT DOCUMENTS

| | | | |
|---|---|---|---|
| 3,120,563 | 2/1964 | Bongard | 260/555 A |
| 3,544,628 | 12/1970 | Hsu | 544/201 |
| 3,697,521 | 10/1972 | Van Nassau et al. | 544/201 |
| 3,708,536 | 1/1973 | Hillenbrand | 260/555 A |
| 3,723,430 | 3/1973 | Kokubo et al. | 544/201 |
| 3,936,500 | 2/1976 | Kaasenbrood et al. | 260/555 A |
| 3,952,055 | 4/1976 | Mavrovic | 260/555 A |
| 4,033,928 | 1/1977 | Heunks | 260/555 A |
| 4,036,878 | 7/1977 | Kaasenbrood et al. | 260/555 A |
| 4,066,693 | 1/1978 | Venderbos | 260/555 A |
| 4,086,271 | 4/1978 | Mavrovic | 260/555 A |
| 4,088,685 | 5/1978 | Mavrovic | 260/555 A |
| 4,088,686 | 5/1978 | Mavrovic | 260/555 A |
| 4,094,903 | 6/1978 | Mavrovic | 260/555 A |
| 4,308,385 | 12/1981 | Goorden | 544/201 |

*Primary Examiner*—John M. Ford
*Attorney, Agent, or Firm*—Cushman, Darby & Cushman

[57] ABSTRACT

An improved process for the preparation of melamine from urea or thermal decomposition products thereof wherein ammonia, carbon dioxide, and water vapor are condensed at a pressure of between about 0.5 and 70 bar to form an aqueous solution of ammonium carbamate, and such solution is increased in pressure to at least 100 bar and heated prior to being introduced into a urea synthesis zone wherein at least a portion of the ammonium carbamate is converted into urea. The aqueous solution of ammonium carbamate is heated sufficiently to decompose a portion of the ammonium carbamate into ammonia and carbon dioxide to form a gas-liquid mixture for introduction into the urea synthesis zone such that the heat released by recondensation of the ammonia and carbon dioxide is at least sufficient to provide all of the heat required for the conversion of ammonium carbamate into urea.

11 Claims, 2 Drawing Figures

PROCESS FOR THE PREPARATION OF MELAMINE

BACKGROUND OF THE INVENTION

This invention relates to an improved process for the preparation of melamine by the conversion of urea and/or thermal decomposition products of urea wherein ammonia and carbon dioxide resulting from the melamine preparation are reprocessed to form urea. In a known process, this ammonia and carbon dioxide is condensed at a pressure of between about 0.5 and 70 bar to form an aqueous ammonium carbamate solution, whereafter the solution is brought to a pressure of at least about 100 bar and urea synthesis temperature whereupon the ammonium carbamate is at least in part converted into urea and water.

Such a process is described in U.S. Pat. No. 3,544,628 wherein the gaseous mixture obtained in the preparation of melamine at relatively low pressures is condensed to form an aqueous ammonium carbamate solution, which is thereafter pumped up to the pressure required for urea synthesis. The high-pressure ammonium carbamate solution is subsequently heated to at least a temperature required for the urea reaction using, for instance, steam. Where no separate feeds of ammonia and carbon dioxide are supplied to the urea reactor in that process, the heat required for the endothermic conversion of ammonium carbamate to urea must be introduced into the reactor from an external source. According to the patent disclosure, this is preferably accomplished by overheating the carbamate feed to a temperature about 5° to 25° C. higher than the desired outlet temperature of the urea reactor. Alternatively, the heat for the urea reaction can be provided by external heating of the reactor, for instance by means of heating coils through which high-pressure steam is passed.

This known process has certain disadvantages which derive from the requirement that heat be introduced into the reactor to provide the heat necessary for the conversion of ammonium carbamate to urea. If the required heat for the urea reaction is introduced by means of a heat exchanger in the feed line to the reactor, problems are encountered with respect to the degree of conversion of the carbamate to urea and water, and/or corrosion of the equipment involved. For proper conversion to occur, the temperature selected should be as high as possible. However, since heat is required for the urea reaction, the temperature within the reactor will drop relative to the temperature of the feed to a less than optimum level. This will be detrimental to the conversion of carbamate into urea. Although it is possible to compensate for this temperature decrease by using a higher than usual urea synthesis feed inlet temperature, this poses problems of increased equipment corrosion. At the higher temperatures then required, such expensive corrosion resistant materials must be used that the investment will approach a prohibitively high level.

The alternative is to install heating elements directly in the reactor. However, this poses very difficult problems with corrosion as well.

DESCRIPTION OF THE INVENTION

The object of the present invention is to provide an improved process for the preparation of melamine, and the subsequent processing of the ammonia and carbon dioxide thus obtained to urea, in which the above-noted problems of reduced conversion and/or increased corrosion can be substantially avoided.

These and other objectives are accomplished in accordance with the improvement of this invention, wherein the ammonia and carbon dioxide from the melamine preparation are condensed to form an aqueous solution of ammonium carbamate, which is then pressurized to at least 100 bar and heated in a manner to decompose at least a portion of the ammonium carbamate present in the solution, resulting in the formation of a gas-liquid mixture which is introduced into the urea synthesis reactor. The amount of carbamate decomposed in said aqueous solution is such that the heat released by the exothermic recondensation of ammonia and carbon dioxide to ammonium carbamate within the reactor is at least sufficient to provide all of the heat required for the endothermic conversion of ammonium carbamate into urea. When carried out in this manner, there is no decrease in temperature (and thus conversion) within the urea synthesis reactor, and the feed to the reactor need be heated only to the temperature required for the synthesis and no means for introducing heat into the reactor, such as heating coils, need be provided.

In carrying out this process, it is desirable that the urea synthesis reactor be maintained at a temperature of at least about 180° C., but preferably not in excess of about 200° C. Taking into account the nature of the feed, an optimum conversion efficiency can be obtained within these limits. To carry out the objectives of the invention, it is further preferred to have the urea preparation take place at a temperature of between about 100 and 200 bar. This is substantially the same pressure as that at which the decomposition of the ammonium carbamate in the pressurized reactor feed takes place.

It is, of course, essential that the carbamate can decompose upon heating in the carbamate-containing reactor feed at the chosen temperature and pressure. Should the carbamate content of this feed be too low for sufficient decomposition of carbamate to take place as required by the invention, then it is possible to incorporate an additional process step whereby the carbamate content of this solution can be raised. Alternatively, this carbamate concentration can be changed by modifying the pressure in certain of the processing steps by which the carbamate solution is prepared as described hereinbelow.

The improved process of this invention is particularly suitable in an integrated melamine-urea installation having a relatively small urea plant which processes only the ammonia and carbon dioxide containing off-gases from the melamine plant as feed. In this case, it is necessary to supplement the urea feed to the melamine plant from an external source.

The improved process of this invention, therefore, provides the distinct advantage of doing away with the necessity of providing additional heat to the reactor either by means of over heating the feed to the reactor or supplying heat directly to the reactor via a heat jacket or coils. These alternatives have the disadvantage of reducing urea conversion and/or increased corrosion as described above. This process also provides a distinct advantage over the known process wherein separate streams of both carbon dioxide and ammonia are directly fed to the synthesis reactor to provide the heat required for the endothermic conversion of ammonium carbamate to urea. Direct feeding of carbon dioxide has the disadvantage that a separate compressor is required.

The specific conditions to be applied in the urea synthesis reactor are known and can be derived from the literature. These conditions are described, for example, in U.S. Pat. Nos. 2,777,877, 3,120,563, and 4,053,508. These patents also indicate various means by which the urea synthesis effluent can be processed into a substantially water-free urea melt or urea granules. It is preferred to prepare a urea melt inasmuch as it can subsequently be directly applied as feedstock for the preparation of melamine.

The urea synthesis effluent is an aqueous solution of urea also containing unconverted ammonium carbamate. This urea synthesis effluent is preferably expanded in one or more pressure stages to atmospheric or subatmospheric pressure, optionally with heating, whereby the unconverted ammonium carbamate decomposes. Each decomposition stage is followed by a gas-liquid separation to form a gaseous mixture containing ammonia and carbon dioxide, and an aqueous product urea stream. Depending on the number of stages, one or more such gaseous mixtures are obtained which can be condensed either separately or together to form one or more solutions of ammonium carbamate.

According to one embodiment of the process of this invention, a gaseous mixture from the last pressure stage of ammonium carbamate decomposition is condensed, optionally while supplying water and discharging heat therefrom. The condensate thus obtained is supplied to the condenser of the next higher pressure stage wherein it is used to assist in the condensation of the gaseous mixture obtained from carbamate decomposition in that higher pressure stage. More specifically, two pressure stages of carbamate decomposition are applied, the first stage being carried out at a pressure of between about 10 and 70 bar, and the second stage at a pressure of between about 0.5 and 7 bar.

Depending on the pressures maintained in the various pressure stages of ammonium carbamate decomposition, and the pressure at which the ammonia and carbon dioxide containing gas mixture from the melamine preparation becomes available, the melamine preparation off-gas can be combined with one of the gaseous mixtures from the carbamate decomposition pressure stages whereafter they are jointly condensed.

According to another embodiment, the ammonia and carbon dioxide containing off-gas from the melamine preparation is condensed separately, and the ammonium carbamate thus obtained is supplied as a solution to the appropriate condenser in one of the carbamate decomposition pressure stages of the urea processing system.

The melamine preparation can be carried out using one of the various known methods as described in the literature. Low or medium-pressure processes, that is, processes for the preparation of melamine at a pressure of between 1 and 25 bar, are carried out in the presence of a catalyst, whereas high pressure processes do not require a catalyst.

Various of the known methods can also be used for separation of the melamine product from the reaction product, which essentially consists of melamine, ammonia, and carbon dioxide. In the low or medium-pressure melamine processes, the melamine is present in the reaction mixture as a gas, and can be recovered by cooling the reaction mixture either using water, or one of the reaction components, such as cooled ammonia gas or a cold gaseous mixture of ammonia and carbon dioxide. In the high-pressure processes, the reaction product can, optionally after expansion to a lower pressure, be cooled with water or an aqueous solution of ammonia and carbon dioxide to recover the product melamine.

When using a separation method for the recovery of product melamine in which water or an aqueous solution is added, a solution or suspension of melamine in a saturated ammonium carbamate solution is obtained. Additionally, there will remain a residual gaseous mixture essentially consisting of ammonia, carbon dioxide, and water vapor. The improved process of the present invention is particularly applicable to processing this gaseous mixture into urea. Optionally, this gaseous mixture may be supplemented with other gaseous mixtures containing ammonia and carbon dioxide originating from the further steps of processing the melamine solution or suspension into dry melamine product.

DETAILED DESCRIPTION OF THE DRAWINGS

Figure 1:
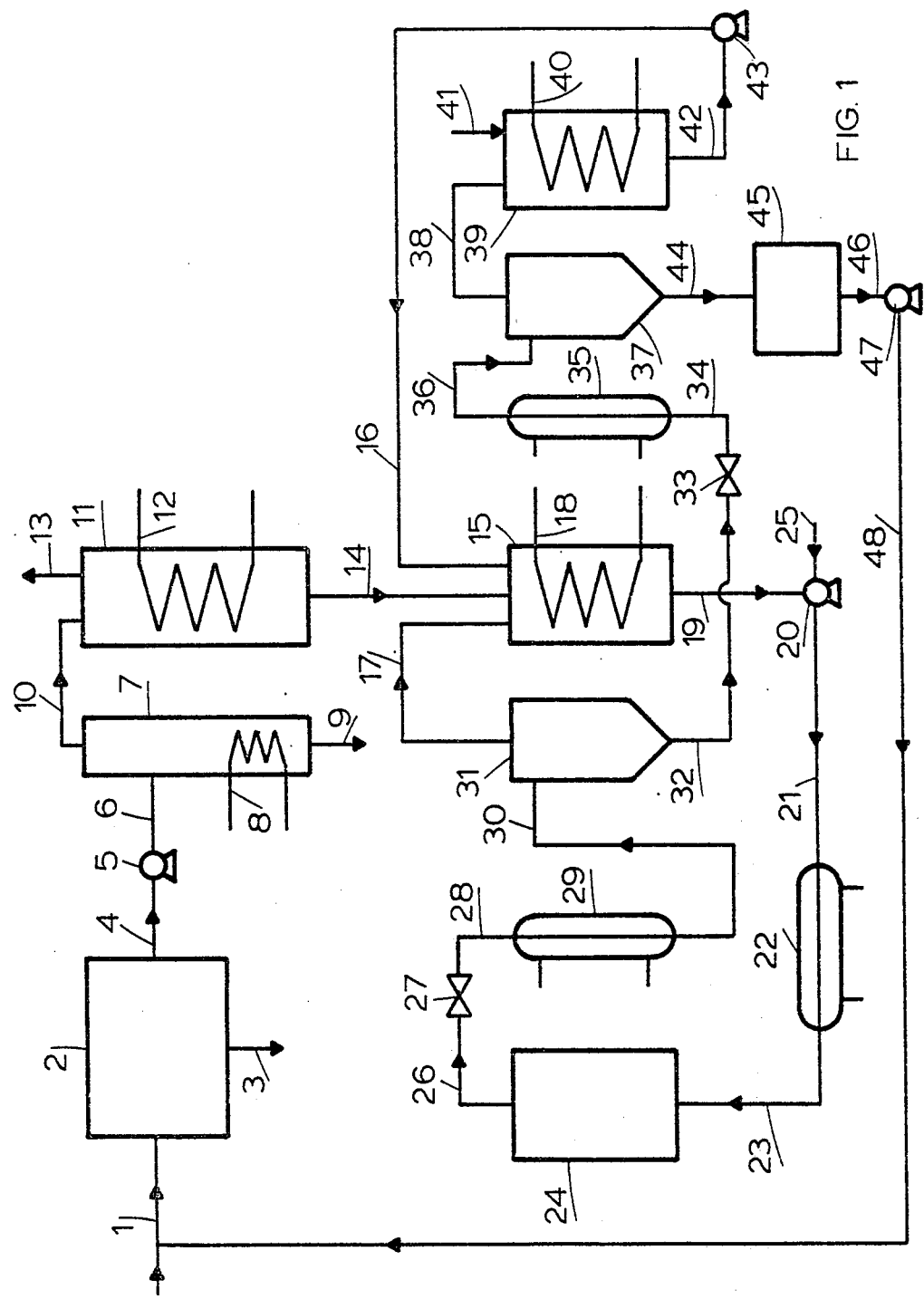
FIG. 1 is a schematic drawing of an integrated melamine and urea preparation installation embodying the improvement of this invention wherein the ammonia and carbon dioxide containing gaseous mixture from the melamine preparation is condensed separately from the gas mixtures derived from the ammonium carbamate decomposition in the urea processing section.

In FIG. 1, molten urea is supplied via line 1 to melamine preparation zone 2 (which is schematically illustrated as simply a block) from which product melamine is discharged via line 3 to storage (not shown). Via line 4, pump 5, and line 6, an ammonium carbamate solution, obtained by condensation of a gaseous mixture remaining after separation of the melamine from the reaction mixture, is supplied to desorption column 7. With the aid of heat supplied through steam coils 8, ammonia and carbon dioxide are desorbed from the solution, and part of the water present evaporates. Practically pure water is discharged from the column via line 9. The gaseous mixture obtained in column 7 passes through line 10 into column 11, wherein it is condensed to form a concentrated ammonium carbamate solution. The heat of condensation is removed from column 11 via cooling coils 12. Any non-condensed gases are discharged via line 13.

The ammonium carbamate solution is supplied to condenser 15 via line 14. Condenser 15 is also fed with a dilute carbamate solution to be described below, via line 16, and a gaseous mixture containing ammonia, carbon dioxide, and water vapor via line 17. This gaseous mixture is condensed in condenser 15 and the heat evolved is discharged by means of cooling coils 18.

The ammonium carbamate solution formed in condenser 15 is introduced into urea reactor 24 via line 19, pump 20, line 21, heater 22, and line 23. Pump 20 brings the solution to the pressure required for the urea synthesis. The ammonium carbamate is heated in heater 22 by means of steam, so that a part of the carbamate decomposes, and the resulting gas-liquid mixture is introduced into urea reactor 24 via line 23. Optionally, additional ammonia for the urea synthesis may be supplied via line 25.

The urea synthesis effluent is discharged from the reactor via line 26, and expanded into a first pressure stage through expansion valve 27, resulting in the decomposition of ammonium carbamate and the formation of a gas-liquid mixture. The gas-liquid mixture is introduced via line 28 into heater 29, in which further decomposition of carbamate takes place, and then via line 30 into gas-liquid separator 31. The gas phase separated in separator 31, consisting primarily of ammonia and carbon dioxide, is subsequently passed to condenser 15 via line 17.

The remaining urea product stream, still containing a small amount of ammonium carbamate, is discharged from the bottom of gas-liquid separator 31 via line 32 and further expanded through expansion valve 33 into a second pressure stage. A further quantity of ammonium carbamate thus decomposes, and the resulting gas-liquid mixture is introduced via line 34 into heater 35 for further carbamate decomposition, and the gas-liquid mixture is passed via line 36 into gas-liquid separator 37. The resulting gaseous mixture is removed from gas-liquid separator 37 via line 38, and is condensed in condenser 39. The condensation in condenser 39 is effected by removing the heat of condensation via cooling coils 40, while water or an aqueous solution may optionally be supplied via line 41. The ammonium carbamate solution obtained in condenser 39 is subsequently pumped to condenser 15 in the first pressure stage via line 42, pump 43 and line 16.

The urea product stream leaving gas-liquid separator 37 is substantially carbamate-free, and is conveyed via line 44 to evaporation section 45 (here schematically depicted as simply a block). In the evaporation section, a substantially water-free urea melt is obtained, which is recycled to the melamine preparation zone 2 via line 46, pump 47, and line 48.

Figure 2:
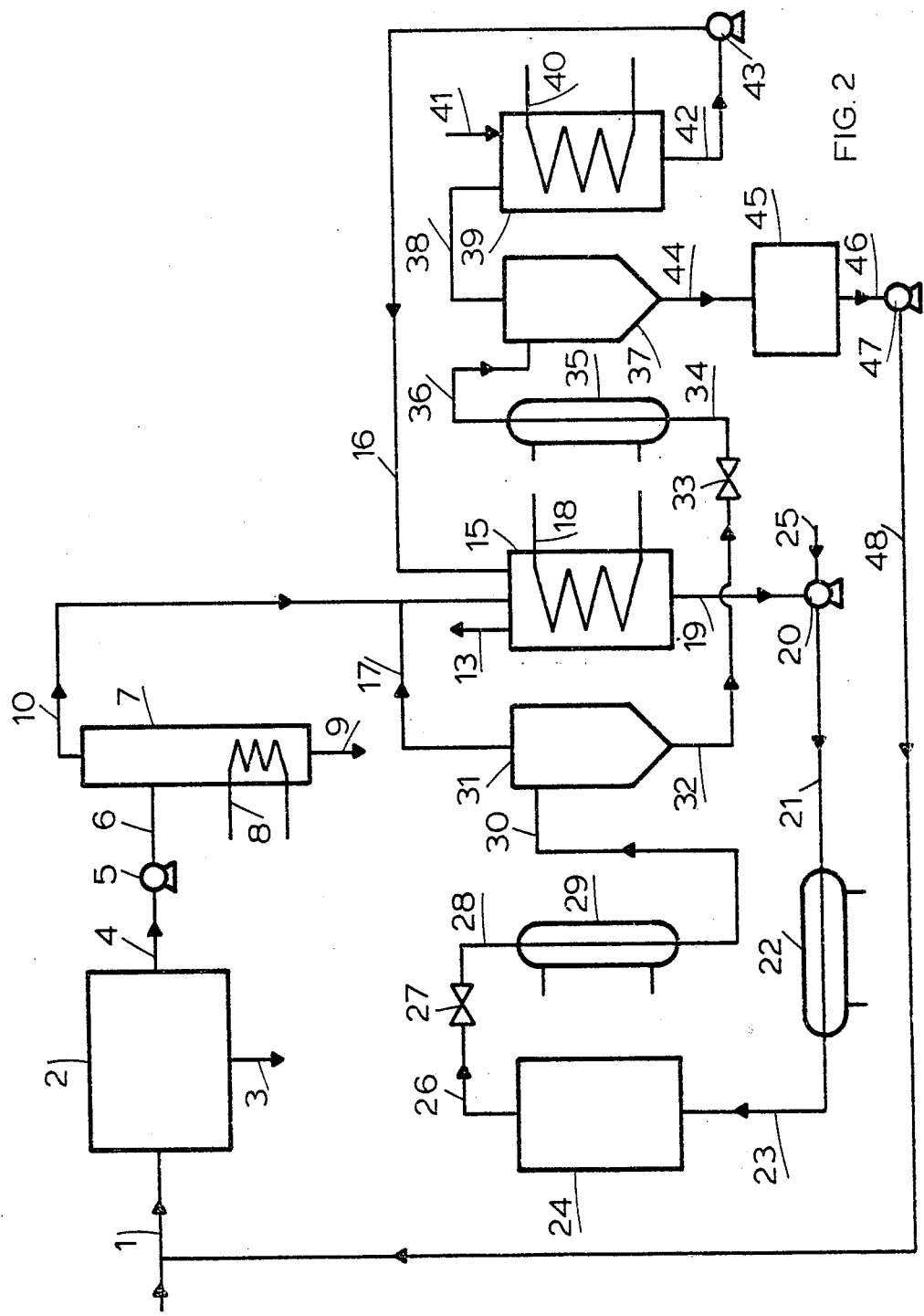
FIG. 2 schematically illustrates an integrated melamine and urea preparation installation embodying the improvement of this invention wherein the ammonia and carbon dioxide containing gas mixture from the melamine preparation is condensed together with a gas mixture derived from decomposition of ammonium carbamate in the urea processing section.

FIG. 2 illustrates a modified embodiment of the process shown in FIG. 1. In FIG. 2, the references figures have the same meaning as in FIG. 1. According to the embodiment of FIG. 2, the ammonia and carbon dioxide containing gaseous mixture derived from the melamine preparation is sent directly from the top of column 7 via line 10 to condenser 15 in the first pressure zone of the urea processing section, wherein it is jointly condensed together with the gas mixture from gas-liquid separator 31. In this manner, condenser 11 shown in FIG. 1 can be deleted. This modified embodiment of FIG. 2 thus has the advantage that less equipment is required.

DETAILED DESCRIPTION OF A PREFERRED EMBODIMENT

The operation of the improvement of this invention will be elucidated by the following example based on the process configuration as shown in FIG. 2.

Melamine preparation zone 2 is supplied with 15.2 tons per hour of urea via line 1 resulting in the formation of 5.0 tons per hour of melamine which is discharged to storage through line 3. The ammonia and carbon dioxide produced in the melamine preparation leave the melamine preparation zone via line 4 and pump 5 in the form of 31.0 tons per hour of an ammonium carbamate solution (35 wt. % ammonia and 19 wt. % carbon dioxide), and is brought up to a pressure of 20 bar.

After desorption in column 7 and condensation in condenser 15, together with the non-converted ammonia and carbon dioxide recovered from the urea processing section, 29.2 tons per hour of a carbamate solution containing 39 wt. % ammonia and 38 wt. % carbon dioxide is brought to a pressure of 150 bar via line 19 and pump 20. This high-pressure solution is thereupon heated to 182° C. in heater 22, resulting in the decomposition of a portion of the ammonium carbamate contained therein. The resulting gas-liquid mixture is fed into urea synthesis zone 24 via line 23.

As a result of the heat evolved from the exothermic recondensation of ammonia and carbon dioxide to form ammonium carbamate, the temperature in the urea reactor rises to 192° C.

The urea synthesis effluent is expanded to a pressure of 20 bar, and in gas-liquid separator 31, a gaseous mixture consisting of water, ammonia, and carbon dioxide is separated from 18.0 tons per hour of a substantially carbamate-free aqueous urea solution containing 46.2 wt. % urea. The urea solution is thereafter expanded to 3 bar and evaporated in the evaporator section, yielding 8.3 tons per hour of molten urea which is sent to the melamine preparation zone via line 48.

What is claimed is:

1. In a process for the preparation of melamine from urea or thermal decomposition products thereof wherein a gaseous reaction mixture containing melamine, ammonia, and carbon dioxide is formed, and wherein said ammonia and carbon dioxide, after separation of melamine therefrom, and water vapor are condensed in a condensing zone maintained at a pressure of between about 0.5 and 70 bar to form an aqueous solution of ammonium carbamate, and said aqueous solution of ammonium carbamate is increased in pressure to at least about 100 bar, heated and introduced into a urea synthesis zone wherein at least a portion of said ammonium carbamate is converted into urea at a pressure of between about 100 and 200 bar to form a urea synthesis effluent containing urea, unconverted ammonium carbamate and water, the improvement essentially comprising heating said aqueous solution of ammonium carbamate from said condensing zone, after being increased in pressure to at least about the pressure in said urea synthesis zone, sufficiently to decompose at least a portion of said ammonium carbamate into carbon dioxide and ammonia, to form a gas-liquid mixture, and introducing said gas liquid mixture into said urea synthesis zone in which said ammonia and carbon dioxide are recondensed to form ammonium carbamate, and ammonium carbamate is converted into urea, wherein the amount of ammonium carbamate decomposed in said aqueous solution and introduced into said urea synthesis zone is such that the heat released by said recondensation of ammonia and carbon dioxide to ammonium carbamate is at least sufficient to provide all of the heat required for said conversion of ammonium carbamate into urea.

2. The process of claim 1 or 2 wherein said urea synthesis zone is maintained at a temperature of between 180° and 200° C.

3. The process of claim 1 wherein urea from urea synthesis zone is processed to form a substantially water-free urea melt, which is thereafter utilized for the preparation of a further quantity of melamine.

4. The process of claim 1 wherein said urea synthesis effluent is heated in at least one pressure stage to decompose ammonium carbamate, and the ammonia and carbon dioxide thus formed are separated from the remaining product urea stream.

5. The process of claim 4 wherein the gaseous mixture of ammonia and carbon dioxide separated from said product urea stream is condensed to form an ammonium carbamate solution.

6. The process of claim 4 wherein said urea synthesis effluent is heated in a plurality of pressure stages so as to decompose ammonium carbamate, and the ammonia and carbon dioxide thus formed are separated as a gaseous mixture from the remaining product urea stream in each stage.

7. The process of claim 6 wherein said gaseous mixtures containing ammonia and carbon dioxide separated from said product urea streams are separately or jointly condensed to form an ammonium carbamate solution.

8. The process of claim 7 wherein said urea synthesis effluent is heated at a pressure of between about 10 and 70 bar in a first pressure stage to form a first gaseous mixture containing ammonia and carbon dioxide and a first product urea solution still containing unconverted ammonium carbamate, and said first urea product stream is heated at a pressure of between about 0.5 and 7 bar in a second pressure stage thereby forming a second urea product stream substantially free of ammonium carbamate, and a second gaseous mixture containing ammonia and carbon dioxide.

9. The process of claim 8 wherein said second gaseous mixture is condensed to form a second aqueous ammonium carbamate solution, and said first gaseous mixture is condensed in the presence of said second ammonium carbamate solution.

10. The process of claim 4, 5, 6, 7, 8, or 9 wherein at least one gaseous mixture obtained by the decomposition of ammonium carbamate present in said urea synthesis effluent is introduced into a condensing zone and condensed together with said ammonia and carbon dioxide from said melamine preparation to form an aqueous solution of ammonium carbamate.

11. The process of claim 4, 5, 6, 7, 8, or 9 wherein at least one gaseous mixture obtained by the decomposition of ammonium carbamate present in said urea synthesis effluent is condensed separate from said condensing zone, and the condensate thus formed is introduced into said condensing zone.

* * * * *